(12) United States Patent
Kozak et al.

(10) Patent No.: US 6,183,648 B1
(45) Date of Patent: Feb. 6, 2001

(54) PROCESS FOR PURIFICATION OF ORGANIC SULFONATES AND NOVEL PRODUCT

(75) Inventors: William G. Kozak, Hatfield, PA (US); Daniel J. Riley, Cedartown, GA (US)

(73) Assignee: Geo Specialty Chemicals, Inc., Cleveland, OH (US)

(*) Notice: Under 35 U.S.C. 154(b), the term of this patent shall be extended for 0 days.

(21) Appl. No.: 09/054,284

(22) Filed: Apr. 2, 1998

Related U.S. Application Data

(60) Provisional application No. 60/043,061, filed on Apr. 4, 1997.

(51) Int. Cl.$^7$ .............................. C02F 1/44; C07C 315/06
(52) U.S. Cl. ...................... 210/651; 210/650; 210/652; 568/31
(58) Field of Search ................................ 210/650, 651, 210/652; 568/31

(56) References Cited

U.S. PATENT DOCUMENTS

| | | | |
|---|---|---|---|
| 2,141,569 | 12/1938 | Tucker et al. ........................... | 106/27 |
| 2,159,806 | 5/1939 | Lenz et al. ........................... | 250/27.5 |
| 3,193,575 | 7/1965 | Nebel et al. ........................... | 260/505 |
| 3,277,162 | 10/1966 | Johnson et al. ...................... | 260/505 |
| 4,465,492 | 8/1984 | Putzar et al. ............................ | 8/589 |
| 4,477,734 | 10/1984 | Graham ................................. | 307/120 |
| 4,767,645 | 8/1988 | Linder et al. ......................... | 427/386 |
| 4,833,014 | 5/1989 | Linder et al. ........................ | 428/308.4 |
| 5,028,336 | 7/1991 | Bartels et al. ....................... | 210/639 |

FOREIGN PATENT DOCUMENTS

| | | | |
|---|---|---|---|
| 1101671 | 5/1965 | (GB) ............................... | D06P/1/84 |
| 1239616 | 9/1968 | (GB) ............................. | B65B/35/50 |
| 1 507 772 | * 1/1976 | (GB) . | |

OTHER PUBLICATIONS

Kirk–Othmer, Encyclopedia of Chemical Technology, Sulfonation and Sulfation, Third Edition, vol. 22, 1983 by John Wiley & Sons, Inc.*

* cited by examiner

*Primary Examiner*—Johann Richter
*Assistant Examiner*—Brian J. Davis
(74) *Attorney, Agent, or Firm*—Rankin, Hill, Porter & Clark LLP

(57) ABSTRACT

A process for producing a low sulfate organic sulfonate/sulfate aqueous solution from a soluble sulfate containing organic sulfonate/sulfate which comprises forming an aqueous solution of organic sulfonate/sulfate; and passing the aqueous solution of the organic sulfonate/sulfate containing the soluble sulfate over a nanofiltration zone at an elevated pressure to form a retentate with a reduced sulfate content and a permeate containing the soluble sulfate and organic material.

17 Claims, 10 Drawing Sheets

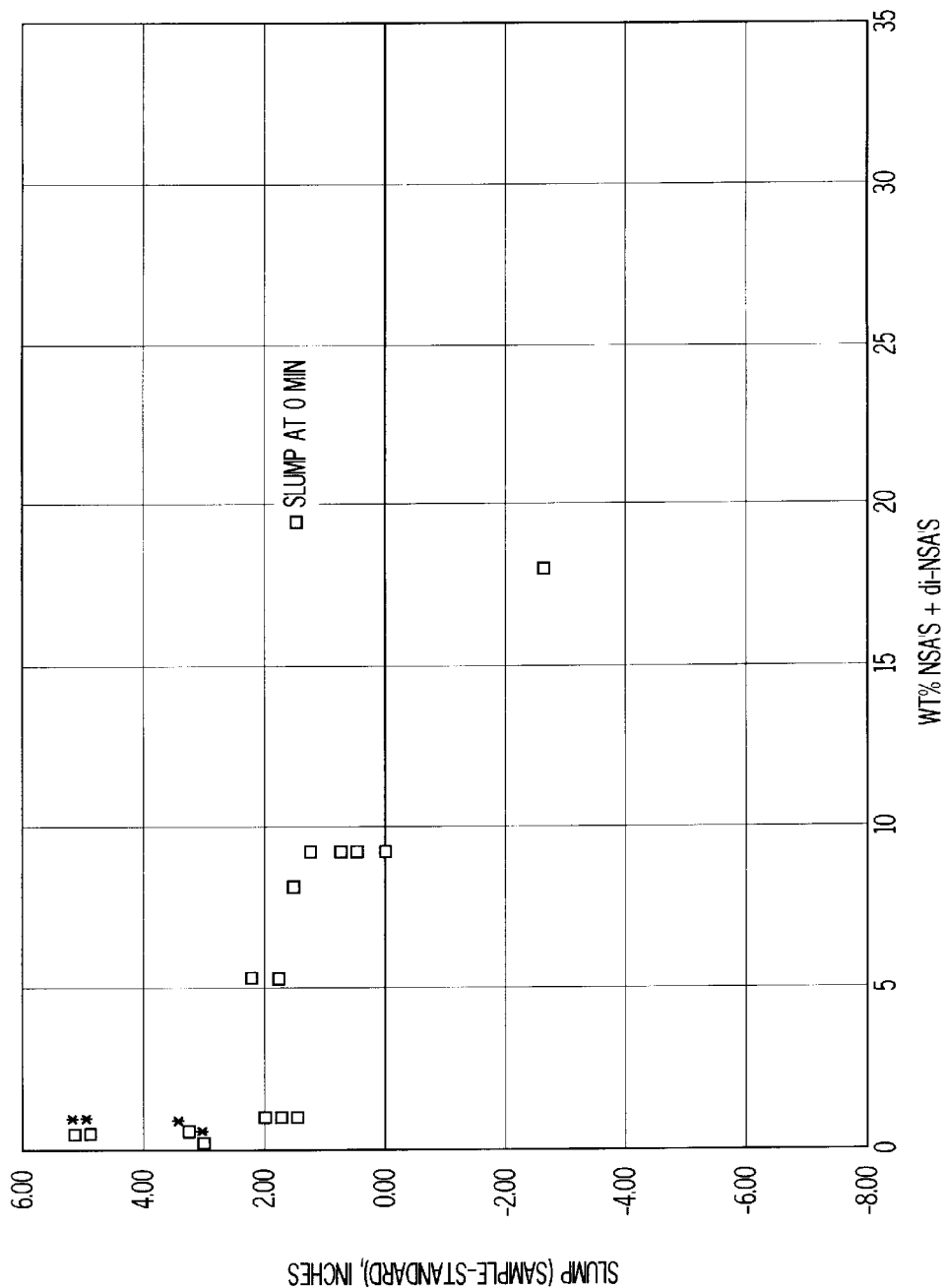

PROCESS FOR PURIFICATION OF ORGANIC SULFONATES AND NOVEL PRODUCT

CROSS-REFERENCE TO RELATED APPLICATION(S)

This application claims priority under 35 U.S.C. §119 from U.S. Provisional Patent Application Ser. No. 60/043,061 filed Apr. 4, 1997

BACKGROUND OF THE INVENTION

The invention relates to a process for removing sulfate ions from organic sulfates and sulfonates and, if required, low molecular weight organic sulfonates/sulfates particularly from aromatic sulfonates and sulfate or aliphatic sulfonate and sulfate compositions. The invention is particularly directed to the removal of sulfate ions from alkyl naphthalenes and alkyl benzene sulfonates, naphthalene sulfonates and the oligomeric materials formed by reaction of the aromatic sulfonates with aldehydes, preferably formaldehyde. Typical materials which can be treated by the process of the present invention are disclosed in U.S. Pat. No. 4,465,492 which is incorporated herein by reference. The organic sulfates or sulfonates or mixtures thereof contain sulfate ions in the form of an acid or salt which results from use of excess sulfonating material used in their preparation. The term organic sulfonates/sulfates as used herein refers to the organic sulfonated or sulfated material or mixtures thereof.

The process for sulfonating naphthalene is described by E. A. Knaggs, "Sulfonation and Sulfation", *Encyclopedia of Chemical Technology*, Vol. 2, p.145 (John Wiley & Sons, Incorporated, New York, New York, 3rd Ed., 1983), the disclosure which is incorporated herein by reference.

The materials which can be treated by the present invention include the condensation polymers of a condensible carbonyl compound and an aromatic sulfonate. Preferred examples of such condensates are formaldehyde condensates of naphthalene sulfonic acid and formaldehyde condensates of lower alkyl substituted naphthalene sulfonic acid. Other examples are aromatic-based carbonyl condensates including condensation products of acetone with naphthalene sulfonic acid or benzene sulfonic acid.

Sulfonated aromatic compounds and particularly sulfonated (alkyl)naphthalenes can be employed in the manufacture of the condensates. The term (alkyl)naphthalenes or (alkyl)benzene refers to naphthalenes and benzenes or their alkyl-containing homologs. However, as an alternative to pre-sulfonation, the naphthalene can be sulfonated during condensation with the aldehyde. Condensation and sulfonation produces a product which is considered a naphthalene aldehyde sulfonic acid or naphthalene sulfonic acid-aldehyde condensate. The processes for preparing the condensates are described in U.S. Pat. No. 2,141,569 (Tucker et al.), issued Dec. 27, 1938, U.S. Pat. No. 3,193,575 (Neville et al.), issued Jul. 6, 1965, and U.S. Pat. No. 3,277,162, Johnson, issued Oct. 4, 1966, the contents of which are incorporated herein by reference. Condensation products generally have a number average molecular weight of from about 1,500 to about 6,000 and a weight average molecular weight of from about 3,000 to about 16,000 and will contain up to about 8 to 30% by weight of non-condensed materials such as mono- and di-sulfonated aromatic materials. Composition with higher and lower number average or weight average molecular weight can be treated to remove sulfate ions from the composition.

The (alkyl)naphthalene sulfonic acid formaldehyde condensation products comprise a mixture of condensation products of (alkyl)naphthalene sulfonic acid and formaldehyde. The condensation products differing for example in the degree of polymerization. The mixture can be separated by size-exclusion chromatography to selectively separate the molecular species according to size. This is one method for obtaining a measure of the degree of polymerization.

The aromatic aldehyde condensates are generally water-soluble or water-dispersible and contain substantial amounts of sulfate (up to about 15 to 20% by weight of the solids) depending upon the ratio of the sulfonating agent to the aromatic compound. Depending upon the commercial use for the material, the level of sulfate in the composition must be reduced. If a high-salt form of the composition is required, the unreacted sulfuric acid is merely neutralized and the condensate containing the neutralized sulfuric acid can be sold for certain uses.

If a low-salt material (less than about 3.0–6.0% by weight of the solids) is required, the sulfate ions must somehow be separated from the aromatic sulfonate aldehyde condensation product. This can be accomplished by neutralizing the unreacted sulfuric acid with an alkaline material such as calcium hydroxide and separating the calcium sulfate formed from the aromatic sulfonate-aldehyde condensation product. However, the water solutions or dispersions generally have a high viscosity and the filtration can be difficult. The mixture of calcium sulfate with the aromatic sulfonate-aldehyde condensation product must also be disposed of. This is an expensive problem because the amount of raw materials that is converted to filter cake is substantial and the filter cake must be disposed of in a hazardous waste material disposal facility. In addition to the aforementioned expenses, the material also carries with it a portion of the aromatic sulfonate-aldehyde condensation product.

In view of the disposal problems and the cost of the raw materials to neutralize the excess sulfate, processes for preparing the aromatic sulfonate aldehyde condensation products are generally optimized to provide the required sulfonation utilizing the minimum amount of excess sulfuric acid. The diagram of a known process requiring neutralization and separation of calcium sulfate for preparing the aryl sulfonate aldehyde condensation products is set forth in FIG. 1.

The presence of the sulfate salts and the unpolymerized and uncondensed aryl mono- and di- sulfonates has a deleterious effect on the use of the condensation products as a cement additive. It would be useful to be able to easily reduce the amount of sulfate and the amount of unpolymerized or uncondensed aryl sulfonates in the composition.

BRIEF DESCRIPTION OF THE INVENTION

According to the present invention, an organic sulfonate/sulfate or particularly an aryl sulfonate or aryl aldehyde sulfonate condensation product with a low sulfate content can be prepared by passing an aqueous solution of a neutralized or acid form of the organic sulfonate/sulfate or particularly an aryl sulfonate or aryl sulfonate aldehyde reaction product through a nanofiltration zone to separate the sulfate ions from the mixture to provide a retentate with a reduced sulfate content and a permeate comprising of primarily sulfate and a significantly lower amount of uncondensed organic sulfonatelsulfate or aryl mono- and di-sulfonates and lower molecular weight oligomers. The permeate is then passed to a separation zone wherein the sulfate is separated from the solution of the organic mono- and di-sulfonates and low molecular weight oligomers thereof. If the sulfate has not been neutralized, the sulfuric acid solution can be concentrated and returned to the sulfonation zone to be mixed with oleum to raise the strength to that required for the sulfonation reaction. The mono- and di-sulfonates and the low molecular weight oligomers can be mixed with the feed to the aldehyde-condensation step or to the feed to the nanofiltration step of the process if a low mono- and disulfonate product is not required.

The invention also comprises the aryl sulfonate aldehyde condensation product with a reduced content of sulfate and aryl mono- and di-sulfonates and low molecular weight oligomers which shows improved properties as a dispersant for forming cement-containing materials such as concrete.

The invention also includes a method for treating a nanofiltration membrane to improve rate of flow of the permeate containing the sulfate and aryl mono- and di-sulfonates and low molecular weight condensation oligomers thereof through the nanofiltration membrane.

DETAILED DESCRIPTION OF THE INVENTION

The process of the invention is particularly useful for removing salts or acids from sulfated or sulfonated water soluble or water disposable organic sulfonatesisulfates. The organic sulfonate/sulfates are known products which can be prepared by methods such as described in U.S. Pat. No. 2,199,806, U.S. Pat. No. 3,849,162, British Patent Specification 1,101,671, British Specification No. 1,239,016 and British Specification 1,507,772. Typical examples are sulfated alkaline oxide adducts, sulfated and partially esterified polyhydric alcohols, alkyl sulfonates, alkyl sulfates, sodium dialkyl sulfosuccinates, alkyl benzene sulfonates, condensation products of (alkyl)naphthalene sulfonic acid and formaldehyde, condensation products of ditolyether formaldehyde and sulfuric acid, condensation products of chloromethylated diphenylene, (alkyl)naphthalene and sulfuric acid, condensation products of mononuclear aromatic compounds, formaldehyde, (alkyl)naphthalene sulfonic acids and optionally sodium sulfite, or condensation products of (alkyl)naphthalene, toluene formaldehyde and sulfuric acid.

The process of the present invention is particularly useful for removing the sulfate and, if required, mono-sulfonates and di-sulfonates from condensation products of (alkyl) benzene and/or (alkyl)naphthalene monosulfonic acids which may be substituted with an alkyl moiety having 1 to 18 and preferably 1 to 10 carbon atoms ((alkyl) aryl sulfonates) and formaldehyde. These dispersants are disclosed in U.S. Pat. No. 4,465,492 to Putzer, patented Aug. 14, 1984, which discloses other materials which can contain sulfate, which can be removed from the composition.

The known processes react the aryl compound with sulfuric acid to form the sulfonate which is reacted with an aldehyde such as formaldehyde to form a condensation product. The process can be carried out in a single step. Excess sulfuric acid is used, generally from about 5% to 50% excess. If a low salt product is required the sulfuric acid is neutralized with lime to form calcium sulfate which is filtered from the liquid mixture, the sulfonate neutralized with sodium carbonate to precipitate residual calcium as calcium carbonate and the neutralized product is again filtered and packaged for sale.

Figure 1:
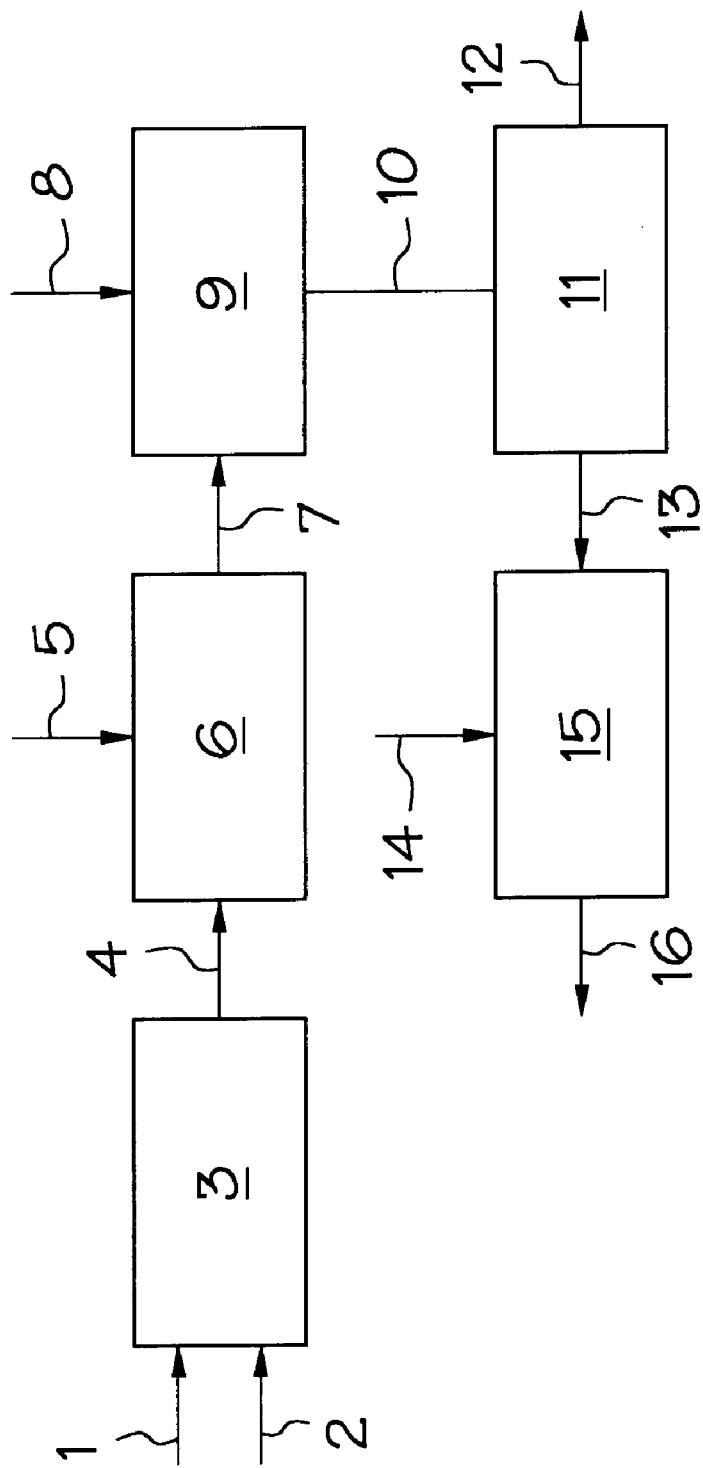
FIG. 1 is a diagrammatic representation of a process for preparing aryl sulfonate aldehyde condensation products with a reduced amount of sulfate in the mixture.

The prior art process is shown in FIG. 1. Sulfuric acid or oleum are fed through line 7 level and the aromatic compound to be sulfonated is introduced in reaction zone 3. A sulfonate is formed and a mixture comprising the aromatic sulfonate and excess and unreacted sulfuric acid passes to condensation zone 6 through line 4. An aldehyde such as formaldehyde and water is introduced through line 5 and is mixed with the sulfonate mixture in reaction zone 6 to form the condensation product. The condensation product passes through line 7 to neutralization zone 9 where it is neutralized and diluted with water by a lime slurry introduced through line 8. Calcium sulfate is precipitated and the mixture passes to filter 11 through line 10. The filter cake mixed with occluded condensation product is sent to waste disposal through line 12 and the liquid filtrate passes to neutralization zone 15 through line 13. In neutralization zone 15 if a low sodium, low calcium product is required, the condensation product is mixed with sodium carbonate introduced through line 14, filtered, and the concentration adjusted to sales specification. The product ready for packaging and shipping is removed through line 16.

The process of the invention will be described in relation to removal of sulfate from (alkyl) naphthalene sulfonate and a condensation product of (alkyl) naphthalene sulfonate with formaldehyde.

The sulfonation of (alkyl) naphthalenes and the condensation of sulfonated (alkyl) naphthalenes with formaldehyde are well known and the sulfonation process described in relation to FIG. 1. Aromatic material such as (alkyl) naphthalene can be sulfonated by contact with oleum or sulfuric acid. If a condensate is to be formed, the sulfonated (alkyl) naphthalene is then reacted with an aldehyde, preferably formaldehyde to form the condensation product. In an alternative method, the sulfonation and condensation can be carried out in a single step to produce a sulfonated (alkyl) naphthalene formaldehyde condensation product.

In the process, to ensure substantial sulfonation of the aromatic components, an excess of oleum or sulfuric acid is utilized. The excess sulfuric acid does not affect the condensation reaction, but it can be detrimental to the end uses for the product. By the process of the invention, the unreacted sulfate moieties and if required, the unpolymerized (alkyl) naphthalene sulfonates can be separated from the reaction mixture.

Figure 2:
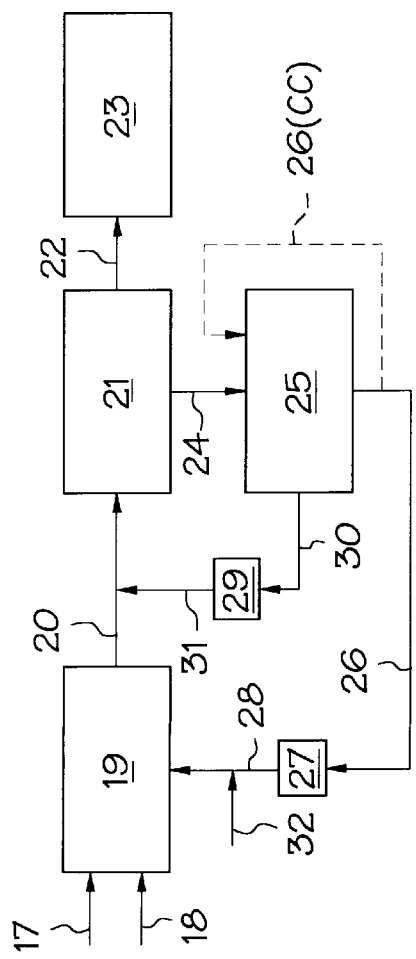
FIG. 2 is a diagrammatic representation of the process of the present invention.

The reaction to form the condensation products of the (alkyl) naphthalene sulfonates is an acid process and is carried out in the presence of the excess sulfuric acid and water. For use, the condensation product is generally neutralized with an alkaline material such as sodium hydroxide or sodium carbonate. Along with neutralization of the condensation product, the unreacted sulfuric acid and monomeric sulfonates are also neutralized. The neutralized product or the unneutralized product can be treated by the process of the invention to remove the sulfate and monomeric (alkyl) naphthalene mono- and di-sulfonates from the reaction mixture. The process of the invention is shown diagrammatically in FIG. 2.

The (alkyl) naphthalene, enters sulfonation-condensation zone through line 17. Formaldehyde is introduced through line 18 and sulfuric acid through line 28. The sulfuric acid is added through line 28. It is a blend of oleum which enters through line 32 and lower concentration recycled sulfuric acid from the acid concentration zone 27. The (alkyl) naphthalene is sulfonated and condensed to form the condensation product. The condensation product contains the excess unreacted sulfuric acid. A solution of the (alkyl) naphthalene-formaldehyde condensate in water containing from about 20% to 60% by weight (alkyl) naphthalene-formaldehyde condensate passes to nanofiltration zone 21 through line 20.

In nanofiltration zone 21 the solution of (alkyl) naphthalene sulfonate-formaldehyde condensation product is passed through a nanofiltration apparatus at pressure in the range of 150 to 700 pounds per square inch gage and a temperature of 35° to 85° C. to form a retentate with a reduced sulfate content and, if required, a reduced content of mono- and di-sulfonated (alkyl) naphthalene. Permeate which is obtained near the end of the diafiltration cycle (which is sufficiently low in sulfate) can be used as water make up early in the next diafiltration batch through line 26a. The unrecycled permeate passes to the separation zone.

If the nanofiltration unit is sufficiently large, the sulfate concentration can be reduced to a sufficiently low level with one pass through the nanofiltration apparatus. However, water must be added to maintain the concentration of the condensation product in the range of not higher than about 40%–60% by weight of the solution. For solutions or dispersions of materials other than (alkyl) naphthalene sulfonate-formaldehyde condensation products, higher concentration may be used.

A preferred method for carrying out the nanofiltration is by a diafiltration method wherein the (alkyl) naphthalene sulfonate-formaldehyde reaction product is circulated over the nanofiltration membrane and sufficient water is added to maintain the concentration of the (alkyl) naphthalene sulfonate-formaldehyde condensation product in the range of 30% to 45%, preferably 35% to 40% by weight of the solution. When the sulfate level has reached a required level the nanofiltration is discontinued. The (alkyl) naphthalene sulfonate-formaldehyde condensation product is in the retentate (the material which does not pass through the membrane). The retentate with the reduced sulfate content is ready for packaging and sale. The retentate passes from nanofiltration zone 21 through line 22 to storage zone 23.

The permeate (the material which passes through the nanofiltration membrane) flows to a permeate treatment zone 25 through line 24.

In permeate treatment zone 25 the sulfate is separated from the permeate to form a sulfate containing aqueous stream and an aqueous stream containing the (alkyl) naphthalene mono- and di-sulfonates and low molecular weight reaction products. The sulfate-containing aqueous stream can be an acid stream which passes to acid concentration zone 27 through line 26. The concentrated sulfuric acid can be mixed with oleum and introduced into the sulfonation condensation zone as a portion of the acid feed through line 28. Oleum make-up is introduced through line 29.

If the nanofiltration is carried out on a non-neutralized (acid) mixture, sulfuric acid can be separated from the permeate by an electrodialysis process which would constitute permeate treatment zone 25.

Electrodialysis is a known process and utilizes cationic and anionic membranes and a direct current electric field to separate ions from an aqueous stream. The (alkyl) naphthalene mono- and di-sulfonates and oligomer condensation products are too large to pass through the membrane efficiently and the sulfate ions are separated from the permeate to form dilute sulfuric acid with less than about 5% by weight and preferably less than about 1% by weight of organic sulfonatelsulfate material on a water free basis. The dilute sulfuric acid passes to acid concentration zone 27 through line 26. After concentration, the sulfuric acid is mixed with oleum make-up which enters through line 32 and introduced into sulfonation-condensation zone 19.

The treated permeate with the reduced sulfuric acid content is passed to treated permeate storage zone 29 through line 30. The low molecular weight oligomers and the (alkyl) naphthalene mono- and di-sulfonates can be mixed with the sulfonation-condensation reaction product from zone 19 to be condensed or can be introduced into the feed to the nanofiltration zone when a product with low concentration of monomers and oligomeric materials is not required. The process can be operated with substantially no waste or minimal amounts of waste which must be discarded in a hazardous waste disposal facility.

If the sulfonation-condensation reaction product is neutralized before the nanofiltration treatment sulfuric acid can be recovered in a bipolar electrodialysis zone and the mono- and di-sulfonated (alkyl) naphthalene and the oligomers can be returned to the feed to the nanofiltration zone and the caustic stream from the bipolar electrodialysis unit can be returned to the condensates product neutralization step.

In an alternate procedure when the feed to the nanofiltration zone has been neutralized, the sulfate can be separated from the mono- and di-sulfonated (alkyl) naphthalene and low molecular weight organic sulfurate/sulfate products in the permeate by passing the permeate through an ion exchange zone containing an alkaline ion exchange medium and preferably a weakly alkaline ion exchange medium. The sulfate salt passes through the ion exchange zone. The mono- and di-sulfonated (alkyl) naphthalene and the oligomers in the permeate will preferentially remain with the ion exchange material and can be regenerated from the ion exchange material with an aqueous alkaline material and mixed with the feed to the nanofiltration zone.

When ion exchange is utilized to separate the sulfate from the mono- and di-sulfonated (alkyl) naphthalene and the oligomers in the permeate from a neutralized reaction mixture, the sulfate is in the form of a salt and the liquid stream is discarded. Since the organic materials in the stream are present in only small amounts, the effluent containing the sulfate salts is generally suitable for discharge to municipal sewerage treating systems.

NANOFILTRATION

In the first step of the process of the present invention, the neutralized or unneutralized organic sulfonatelsulfate product or condensation reaction mixture is treated in a nanofiltration zone.

Nanofiltration is a known operation in which a solution or dispersion of a material to be treated is passed over a nanofiltration separation membrane at a pressure which is generally in the range of from about 150 to about 700 psig (depending upon the strength of the membrane) to cause the sulfate and the lower molecular weight materials to pass through the membrane along with the water to form a permeate and an aqueous phase which does not pass through the membrane, which is known as a retentate. Upon passage through the nanofiltration module, the retentate has a lower concentration of the sulfate and if required, lower molecular weight (alkyl) naphthalene sulfonates and oligomers thereof than the feed entering the nanofiltration module.

Nanofiltration is more generally carried out at a moderate pressure in the range of from about 200 to about 500 pounds per square inch gauge pressure drop across the membrane. An increase in pressure usually increases the rate of permeate formation. However, the pressure which can be utilized is determined by the temperature, nature of the particular nanofiltration membrane and the particular design of the nanofiltration apparatus.

The reaction product is passed through the nanofiltration apparatus at as high a temperature as possible considering the nature of the nanofiltration membrane and the pressure utilized in the filtration operation. The high temperatures are useful in that the (alkyl) naphthalene sulfonate formaldehyde condensation product provides a viscous solution at concentrations in the range of above about 30% by weight of the (alkyl) naphthalene sulfonate formaldehyde condensation product. Generally, temperatures in the range of from about 40° C. to about 80° C., preferably 70° C. can be utilized when the process is operated with a suitable membrane.

A nanofiltration membrane suitable for use in the method of the present invention comprises a hydrophilic membrane which is generally crosslinked and has ionic groups, which is supported on a porous polymeric material which can be further supported on a substrate which provides strength to the composite membrane. The membrane is preferably asymmetric in that both sides of the supporting substrate are not the same. Only the face of the membrane which contacts the aqueous phase to be treated comprises the thin layer of hydrophilic crosslinked ionic polymer material. The nanofiltration membranes are generally provided in certain grades which have been manufactured to reject passage of molecules above a critical molecular size. That is, membranes can be provided which reject molecules with a molecular weight above about 200 to membranes which pass molecules having a molecular weight of less than several thousand. In this context of this invention, molecular weight is used to indicate molecular size, but molecular size is a more appropriate term. However, for the process of the present invention, a nanofiltration membrane having a molecular weight cut-off in the range of from about 150 to about 1000 and preferably about 200 to about 500 can be utilized in the practice of the present invention. The molecular weight cut-off for the nanofiltration membrane useful in the practice of the present invention is determined by the nature of the aqueous solution from which the sulfate is to be removed, and in particular the molecular weight of the component which is to be retained in the retentate and the largest molecular weight of the molecules which are passed through the membrane and collect in the permeate. A membrane must also be selected with regard to the pH of the aqueous solution from which the sulfate is to be removed.

Typical membranes for use in nanofiltration and ultrafiltration processes are disclosed in U.S. Pat. No. 4,767,645 to Linder et al., U.S. Pat. No. 4,477,734 to Linder et al., U.S. Pat. No. 4,833,014 to Linder et al., U.S. Pat. No. 5,028,336 to Bartels et al., and U.S. Pat. No. 5,049,282 to Linder et al. (The aforementioned patents are hereby incorporated by reference.) The type of membrane which is selected is dependent upon the pH of the aqueous solution to be treated with the nanofiltration unit, the molecular weight cut-off required, and the temperature and pressure at which the nanofiltration is to be carried out. The most critical parameters are the molecular weight cut-off, the pH and temperature requirements for the nanofiltration step.

As used herein the term nanofiltration refers to a process wherein an aqueous solution of an organic sulfonate/sulfate and particularly the condensation product of an (alkyl) aromatic sulfonate with an aldehyde such as formaldehyde is passed over a membrane having a molecular weight cut-off in the range of from about 150 to about 1000 and preferably from about 200 to about 700 and more preferably from about 200 to about 500. As is well understood in the art, nanofiltration is carried out at a moderate pressure drop across the membrane in the range of from about 200 to about 500, and preferably from about 250 to about 420 pounds per square inch. The pressure drop through the nanofiltration module is generally within the range of 50 to 200 psig and preferably about 50 to about 100 psig. The term nanofiltration as used herein overlaps with ultrafiltration at the high molecular weight cut-off range and reverse osmosis at the low molecular weight cut-off range. As these terms are used in the art there is generally an overlap at each end of the molecular weight cut-off range. Membranes with higher molecular weight cut-off ranges can be used if higher molecular weight oligomers are to be separated from the aqueous phase. A description of the various parameters utilized and the nomenclature for filtration is set forth in the table, THE FILTRATION SPECTRUM by Osmonics, Incorporated, which is incorporated herein by reference.

In operation of the nanofiltration step, the membrane is arranged so that the aqueous solution to be subjected to nanofiltration is passed over the hydrophilic surface of the membrane at a pressure in the range of from about 100 to about 700 pounds per square inch, where the compounds with a molecular weight below the molecular weight cut-off range permeate pass through the membrane along with a portion of the water in the solution. The material which permeates through the membrane is noted as a permeate, while the material which does not pass through the membrane is noted as the retentate. In the practice of the present invention, the sulfate ions and a portion of the water pass through the membrane and are removed with the permeate. The uncondensed (alkyl) aryl sulfonates with a molecular weight below or slightly above the molecular weight cut-off and low molecular weight oligomers also pass through the membrane at a significantly lower rate and can be collected in the permeate.

The composite membrane useful in the practice of the present invention may be utilized in various configurations. For example, it is possible to utilize the composite membrane arranged in a plate and frame configuration in which the separating layers may be mounted on a porous support layer with a carrier layer or use the form of hollow tubes.

Figure 5A:
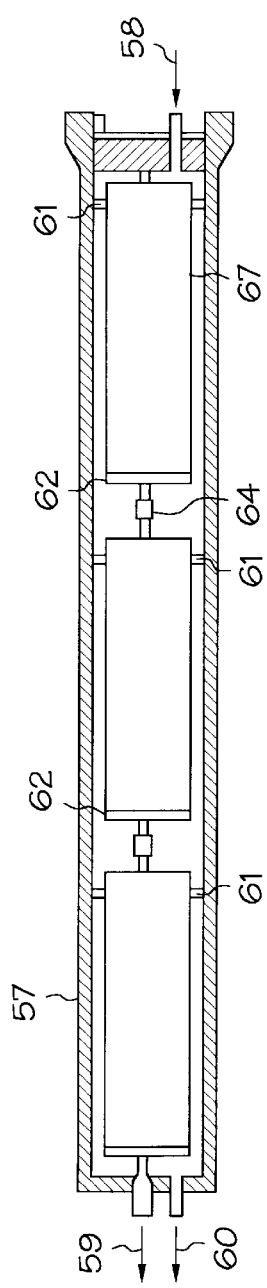
FIGS. 5(a) and (b) are drawings of a spinal wound nanofiltration device.
Figure 5B:
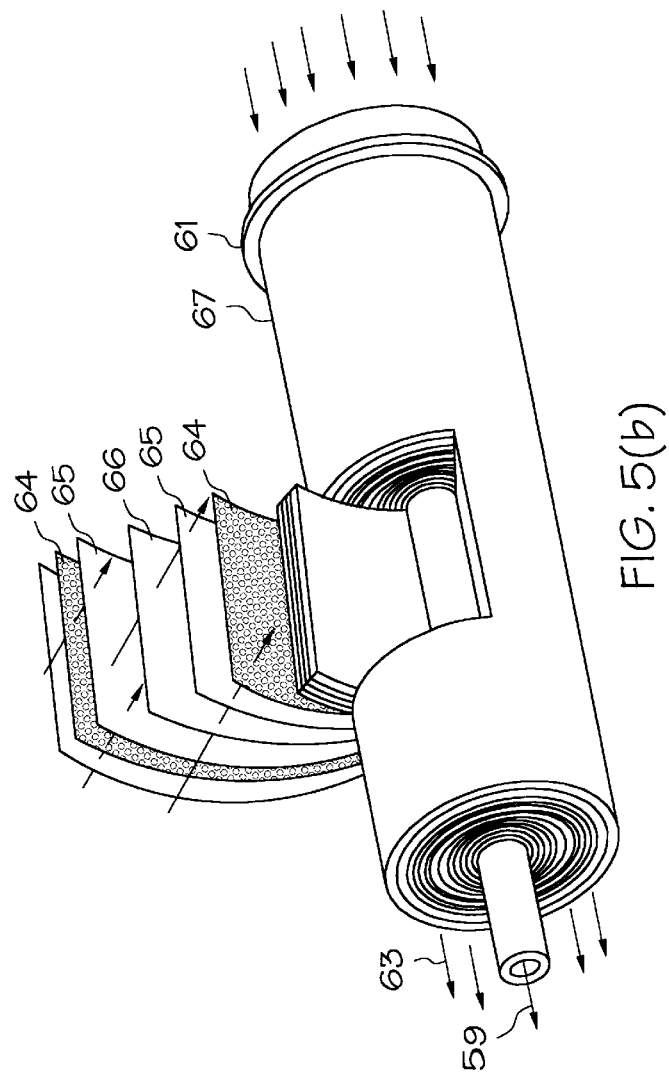

It is also possible to utilize a spiral configuration module which includes a separating layer membrane mounted on a porous support layer and a carrier layer, the assembly being typically folded and bonded or sealed along three edges with an open edge to form a bag-like unit which preferably has the separating layer on the outside. A spacer serving as a permeate discharge channel is placed within the bag-like unit. A discharge channel projects from the end of the unit. A spacer is provided on the outer face of the bag-like structure which is to contact the aqueous solution subject to nanofiltration. An outlet from the bag-like layer is then joined to a central discharge conduit which passes out of the nanofiltration unit to provide an exit for the permeate from the nanofiltration zone. The bag-like structure is then wound around the conduit with the spacer element providing a space between layers of the spiral wound element through which the aqueous phase, being subject to the nanofiltration, can flow past the surfaces of the membrane. The hydrophilic crosslinked ionic surface is exposed to the aqueous phase, from which the sulfate is to be removed under elevated pressure. The spiral wound unit can be formed from a number of bag-like units which are attached to the central conduit then wound in a spiral fashion. The spiral wound element is then mounted in a shell with a baffle-like seal between the inner surface of the pressure vessel shell and the outer surface of the spiral wound nanofiltration module. The baffle-like seal is useful to insure that the liquid which is to be nanofiltered does not bypass the nanofiltration module. A drawing of a spiral wound nanofiltration unit is shown in FIGS. 5(a) and (b). FIG. 5(a) is a schematic drawing of an assembled spiral wound nanofiltration unit.

Three spiral wound membrane modules 67 are arranged in pressure vessel 57. The feed solution enters through conduit 58 and passes between the leaves formed by membrane 65 and permeate space 66 which are sealed at their edges. The leaves are separated by spacers 64. Flow of feed material is through spacer 64. Flow around module 67 is prevented by seal 61. The permeate collects in conduit 59 and is removed from the rest. The retentate flows out of pressure vessel 57 through line 60. Antitelescoping fittings 62 prevent the module intervals (spacers, 64, and membranes, 65) from being forced by the pressure drop out the end of module 67. The pressure drop for flow through the spiral wound unit can be in the range of 50 to 100 psi. A coupling 68 joins several modules 67 in the pressure vessel.

The pressure drop between the retentate side of the membrane and the permeate side of the membrane is generally in the range of 200 to 500 psi depending on the structure of the membrane.

During the ultrafiltration process, a portion of the water is transferred through the nanofiltration membrane along with the sulfate ions. Since the permeate contains a relatively low concentration of the sulfate ions, it is generally necessary to add additional water to the retentate to insure that the viscosity does not increase to the point that the material does not readily flow across the surface of the membrane or that the permeate becomes so concentrated in the sulfate moieties that the membrane plugs and prevents the nanofiltration process from taking place.

It is generally necessary to introduce water into the solution to prevent the viscosity from increasing to the point that the material does not readily flow through the nanofiltration zone. The solution can be recirculated through the nanofiltration zone and water added to maintain the solution at a useful concentration; this type of process is known as diafiltration. The amount of water added to the solution is sufficient to maintain the solution at a concentration in which the viscosity does not interfere with the nanofiltration process.

After the concentration of the sulfate ions in the aqueous phase approaches the required level, the addition of water can be suspended or reduced and the concentration of the (alkyl) aryl sulfonate aldehyde condensation product in the solution can be increased.

If the nanofiltration unit is relatively small, the feed stream is recirculated through the nanofiltration zone and the volume of the feed stream is maintained constant by the addition of water to the recirculating feed stream.

In nanofiltration of (alkyl) aryl sulfonate condensation products, the concentration of the sulfate ions in the permeate increases as the concentration of the (alkyl) aryl sulfonate aldehyde condensation product in the retentate increases. However, at a concentration in the range between about 40 and 45% by weight of the (alkyl) aryl sulfonate aldehyde condensation product the solution becomes viscous and the concentration of sulfate in the permeate becomes so high that the membrane becomes plugged and further nanofiltration is not possible or proceeds so slowly that the process is not economically useful.

Figure 3:
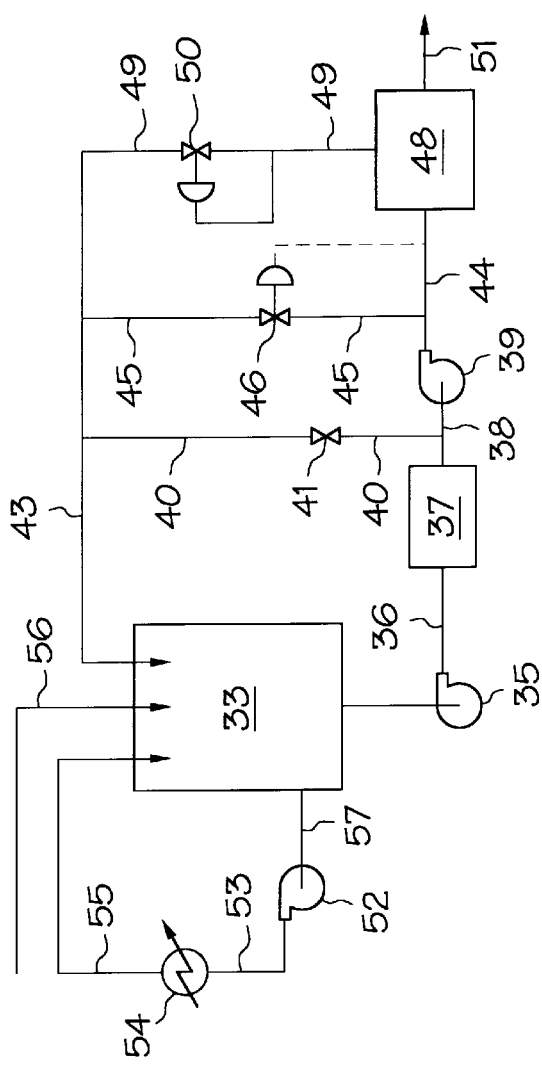
FIG. 3 is a diagrammatic representation of the nanofiltration process utilized in the examples.

In operation of the nanofiltration step, it has been found useful to operate at a temperature in the range of from about 35° C. to about 80° C., preferably 35° C. to about 60° C. with a pressure drop across the membrane in the range of from about 200 to about 400 pounds per square inch at a concentration of the (alkyl) aryl sulfonate aldehyde condensation produce in the range of about 30 to about 40% by weight. In this range, the permeate contains a high percent of the sulfate ion and the sulfate ion is rapidly removed from the retentate. A diagrammatic representation of the nanofiltration apparatus used in the examples of the nanofiltration step is shown in FIG. 3.

After the sulfate ions have been reduced in the retentate to the required level, if the retentate has not been neutralized before or during the nanofiltration operation, the retentate can be neutralized and prepared for utilization.

The (alkyl) aryl sulfonate aldehyde condensation products are generally sold as liquid solutions or dry powders. If a dry powder is required, the neutralized retentate can be spray-dried to form a powder material which is readily soluble in water. The process has been described in relation to an (alkyl)aryl sulfonate-aldehyde condensation product but can be applied to the organic sulfonate/sulfate products The permeate from the nanofiltration zone is then passed to a permeate treatment zone where the sulfate is separated from the organic material which may have passed through the membrane as a portion of the permeate. The method for separating the sulfate ions from the organic material in the permeate is dependent upon whether the sulfate ions are in the acid form or as a sulfate salt. If the sulfate is present in the form of sulfuric acid, that is, the sulfate has not been neutralized, the sulfate can be separated from the organic matter in the permeate by means of an electrodialysis process. Electrodialysis is well known. In an electrodialysis process, the permeate from which the sulfate is to be removed is passed through a cell having an anode, cathode and alternating anionic and cationic membranes separated by thin spacers. The cells are arranged in a stack of at least three cells with the permeate introduced in alternate cells and water introduced into alternate cells. An electrolyte solution is generally introduced into cells at the ends of a stack adjacent to the electrodes Direct current with the positive electrode providing current to the side having the anionic membrane and the negative pole providing current to the side with the cationic membrane. The membranes are generally arranged with a very narrow space between the cationic membrane and the anionic membrane and are arranged in stacks with alternating cationic and anionic membranes.

The permeate is passed into alternate cells and water is passed into alternate cells between the cells to which the permeate is introduced. When the direct current is applied to the stack of cells, the anionic constituents primarily sulfates pass through the anionic membrane into the water stream on the opposite side of the membrane and the cationic materials protons pass through the cationic membrane to the aqueous phase on the opposite side of the membrane. By this method, the sulfate is separated from the aqueous phase and the organic materials. The anionic membrane is selected so that the anionic (alkyl) aryl sulfonate containing materials do not readily pass through the anionic membrane.

The operation of an electrodialysis apparatus is disclosed in Kirk-Othmer, *CONCISE ENCYCLOPEDIA OF CHEMICAL TECHNOLOGY*, pages 406 and 407 (Wiley & Sons 1985) which reference is incorporated herein by reference. The electrodialysis process is also described in *Chemical Engineers' Handbook*, Fifth Edition, Robert H. Perry, consultant and Cecil H. Chilton, Senior Advisor, McGraw-Hill Book Company, published 1973, pages 17–52 through 17–58, which reference is incorporated herein by reference.

The sulfuric acid which has passed through the anionic membrane can be concentrated to 50 to about 80% by weight and returned to the sulfonation process mixed with oleum for forming the (alkyl) aryl sulfonates.

The permeate from which the sulfate has been removed in the acid form can be recycled to the feed to the condensation zone or fed to the nanofiltration unit. If a nanofiltration retentate material with a low content of (alkyl) aryl sulfonate monomeric material is required, the retentate with the monomeric (alkyl) aryl sulfonates must be recycled to the condensation zone or but must be separated and introduced into the feed to the nanofiltration unit when the product is not required to contain only small amounts of the monomeric (alkyl) aryl sulfonate materials.

If the sulfate ions in the permeate have been neutralized and a salt such as sodium sulfate is present in the permeate, it is difficult to separate the sulfate from the organic material in a form which can be recycled to the step in which the sulfonation is carried out. If an electrodialysis unit is utilized, an aqueous stream containing sodium sulfate is formed which must be discarded since it is difficult to recover the sodium sulfate. However, since the amount of organic material in the sodium sulfate stream is relatively low, it is at times possible to discard the sodium sulfate to a municipal sewage treating facility without payment of an unduly large surcharge. The permeate containing the organic material can then be recycled to the step in which the sulfonation condensation product is neutralized.

In an alternative embodiment, when the sulfate is in the salt form, the permeate containing the sodium sulfate and the (alkyl) aryl sulfonates and low molecular weight condensation product oligomers can be passed through a weakly basic ion exchange material. The ion exchange material will remove the organic sulfonates/sulfates and oligomers from the aqueous stream to provide a stream containing the sodium sulfate. The sodium sulfate can be then discarded since the amount of organic material is relatively low. The organic sulfonates/sulfates and oligomers can be regenerated off the ion exchange material introduced into the neutralization step.

The retentate comprising water and (alkyl)aryl sulfonate aldehyde condensate which contains less than about 3.5% sulfate (dry basis) can be readily obtained. Since the material also contains a lower concentration of mono-and di-sulfonated material it has improved dispersing ability over materials prepared by lime/carbonate precipitation process. About 8% by weight of the solid material of mono- and di-sulfonated (alkyl) aryl sulfonates and low molecular weight oligomers has been found particularly useful as a dispersant for forming high strength cement and concrete compositions. Preferably, the dispersant contains less than about 0.75% by weight of sulfate and less than about 5% by weight of mono- and di-sulfonated (alkyl) aryl materials. Preferably, the (alkyl) aryl sulfonate aldehyde condensation product contains less than about 0.5% by weight of sulfate and less than about 2.0% by weight of mono- and di-sulfonated (alkyl) aryl sulfonates. Applicants have unexpectedly discovered that the (alkyl) aryl sulfonate aldehyde condensation products containing only these small amounts of the sulfate and mono- and di-sulfonated (alkyl) aryl sulfonates unexpectedly provides a cement or concrete composition in which the slump is high so that the amount of water in the cement or concrete can be reduced to provide a high strength concrete material.

Applicants have also discovered that the nanofiltration membrane, if treated with a weak nitric acid solution followed by treatment with a solution of a chelating agent such as EDTA, substantially improves the rate at which the aqueous phase permeate passes through the nanofiltration membrane and the amount of permeate collected in a set period of time can be substantially increased. That is, the membrane is first treated by passing a solution containing from about 0.05% by weight to about 5% by weight and most preferably from 0.1% to 3% by weight of nitric acid over the nanofiltration membrane for from about one minute to about an hour at room temperature. The nitric acid solution is then washed from the membrane and an alkaline solution of a chelating agent such as NaEDTA is then passed over the nanofiltration membrane. The operation is generally carried out at a high enough pressure that some of the washing solution passes through the membrane and is collected as a permeate. Applicants do not understand the effect but neither washing with a dilute solution of nitric acid nor a dilute alkaline solution of a chelating agent such as NaEDTA alone is sufficient to improve the rate at which the permeate passes through the membrane. The treatment with the nitric acid followed by treatment with the chelating agent does not substantially affect the rate at which the permeate passes through the nanofiltration membrane from a solution such as glucose. Nor does it affect any solute permeability— solute permeability is the ratio of a solute's concentration in the permeate divided by its concentration in the feed. To Applicants' knowledge, the only effect is that the permeation rate through the nanofiltration membrane from the aqueous solution of the (alkyl) aryl sulfonate aldehyde condensation product is increased. The increase is substantial which can amount to a rate of at least three times the rate of the untreated membrane.

EXAMPLE 1

The experimental work with nanofiltration was carried out in an apparatus as shown in FIG. 3. The aqueous feed to the nanofiltration apparatus was stored in tank 33. The feed to the nanofiltration unit passed out of feed tank 33 through line 34 to pump 35. The feed was pumped through line 36 to filter 37 which separates solid particles from the feed. The filtered feed passes from filter 37 through line 38 to high pressure pump 39. High pressure pump 39 raises the pressure on the liquid to 300–700 psig and the feed passes through line 44 to nanofilter 48. The permeate leaves nanofilter 48 through line 51 and passes to storage. The retentate leaves nanofilter 48 through line 49 and backpressure controller 50 and returns to feed tank 33 through line 43. Line 45 with control valve 46 is a relief valve should the pressure in the nanofilter rise above a preset level. The liquid which may pass through line 45 and control valve 46 returns to feed tank 33 through line 43. Line 40 and valve 41 provide or try to provide a positive suction head for pump 39 and a by-pass for the feed ahead of the high pressure pump.

A pump 52 receives feed through line 57, and pumps the feed through line 53, heat exchanger 54 and line 55 to feed tank 33 to control the temperature of the feed in the range of 40° C. to 70° C. Water is introduced into feed tank 33 through line 56 to maintain the level in feed tank 33 and control the concentration of the dissolved material in the feed. We have discovered that the membrane which was used could not satisfactorily process a feed with more than about 45% dissolved solids. The process was particularly sensitive when the feed contained sodium sulfate salt with the high sodium sulphate permeability it is possible to precipitate salt in the membrane and plug the membrane.

The nanofiltration process is also sensitive to the rate at which the solution passes over the nanofiltration membrane. Higher flow rates promote higher permeation rates. Due to the configuration of the spiral wound membrane used in the experiments, it is difficult to determine the velocity of flow of the liquid through the nanofiltration membrane module. The volumatic flow rate was determined by the flow rate of the retentate leaving the nanofiltration unit.

If the feed solution to the nanofiltration device is viscous, higher temperatures in the range of 30° C. to about 80° C. and preferably 40° C. to 70° C. can be used to reduce the viscosity of the feed solution.

High solids concentration can also produce feed solutions with high viscosity. The concentration of solids in the feed can be a limiting factor in nanofiltration. High solids content can produce solutions with high viscosity which cannot be pumped at high flow rates over the nanofiltration membrane. However, when the (alkyl) naphthalene sulfonate aldehyde condensation product solution is subject to nanofiltration, a high concentration of solids in the feed promotes higher sulfate concentration in the permeate. It has been noted as the solids approach the highest concentration permitted by viscosity consideration (42–45% by weight of concentrated product) the sulfate permeability increase to values as high as 8. The nanofiltration process is operated as a balance between high concentrations of solids in the feed stream and reasonable rate of permeate flow and concentration of sulfate in the permeate.

High pressures encourage high permeate flow. It is preferred to use as high a pressure as permissible considering the nature of the nanofiltration membrane, the temperature and the composition of the feed stream. Pressures in the range of up to 200–700 pounds per square inch pressure and preferably 300–500 pounds per square inch are useful if within the structural limitations of the membrane. The pressure drop across the membrane was controlled in the range of about 200 to about 400 psi.

Experiments were carried out for nanofiltration of an (alkyl) naphthalene sulfonate-formaldehyde condensation product using the apparatus shown in FIG. 3 using a 17 ft$^2$ membrane arranged in a spiral configuration. Neutralized product and unneutralized product were treated to remove sulfate from the product. The membrane was an MPS-34 A2 Sel Ro Nanofiltration Membrane with a molecular weight cut-off of 200, manufactured by Kiryat Weizman Ltd of Israel, distributed in the United States by LCI Corporation, P. O. Box 16348, Charlotte, N.C. The membrane had a maximum temperature range of about 70° C. and a maximum pressure rate of 40 atmospheres.

The membrane was received wet containing a preservative. After the membrane was arranged in the pressure shell, the membrane was washed with water and an alkaline ethylene diamine tetraacetic acid (NaEDTA) solution to remove the preservative from the membrane.

The test results for removal of sulfate from a neutralized (alkyl) naphthalene sulfonate-formaldehyde reaction product with a number average molecular weight in the range of about 3,000 to about 4,000 are shown in Table 1. The test results for an unneutralized (acid) (alkyl) naphthalene sulfonate-formaldehyde condensation product with a number average molecular weight in the range of about 3,000 to about 4,000 for batches 24–27 and about 1,500 to about 2,000 for batch 28 as shown at Table 3.

The neutralized condensation product provided permeate flow rates higher than that produced by nanofiltration of the acid unneutralized condensation product. When the concentration of the feed of neutralized condensation product was in the range of 40%–45% percent by weight solids, the permeate flow rate was substantially reduced and at 45% solids the permeate flow had stopped. The membrane had to be washed with water to restore normal operation.

At high feed solids concentration, above about 30–35% by weight, the concentration of sulfate in the permeate was higher than in the feed. The average concentration of sulfate in the permeate is from 2 to 4 times the concentration of sulfate in the feed calculated by initial sulfate concentration plus final sulfate concentration in the feed to the nanofiltration unit divided by two.

The nanofiltration produced an (alkyl) naphthalene-formaldehyde condensation product with a reduced sulfate content which could be as low as 0.1% to 0.2% by weight of the dissolved solids. The content of mono- and di-sulfonate monomers and low molecular weight oligomers in the (alkyl) naphthalene sulfonate-formaldehyde condensation product was also reduced.

Using a membrane with a cutoff point of 200, the weight ratio of sulfate to organic material in the cumulative permeate was typically in the range of about 3:1 to about 5:1 depending upon the percentage of sulfate removed from the feed. Using higher molecular weight cut-off membranes, the amount of organic material in the permeate could be greater than about 33% by weight of the solids in the permeate.

The reduction in the amount of mono- and di-(alkyl) naphthalene sulfonates in the product (retentate) improves the dispersing effect of the product in cement compositions. The improvement provides for an increase in the initial slump and twenty minute slump for concrete. The increase in the slump can be used to reduce the required amount of water to improve the strength of the concrete. Improvements in slump by as much as 50% have been noted. The products of the process are particularly useful for use in ultra high compressive strength applications that is concrete formulations which have compressive strength with range of above 50,000 pounds and particularly above about 75,000 pounds. The composition of the invention cannot be obtained by controlling reactive conditions during synthesis of the (alkyl) naphthalene sulfates—aldehyde condensation.

The permeate is then treated to separate the sulfate from the organic materials in the solution. Applicants have discovered that the sulfate can be separated from the organic material in the permeate by electrodialysis, ion exchange or treatment in a bipolar electrodialysis separation apparatus. Electrodialysis is particularly useful for separating sulfate in the form of sulfuric acid from the permeate.

Figure 7:
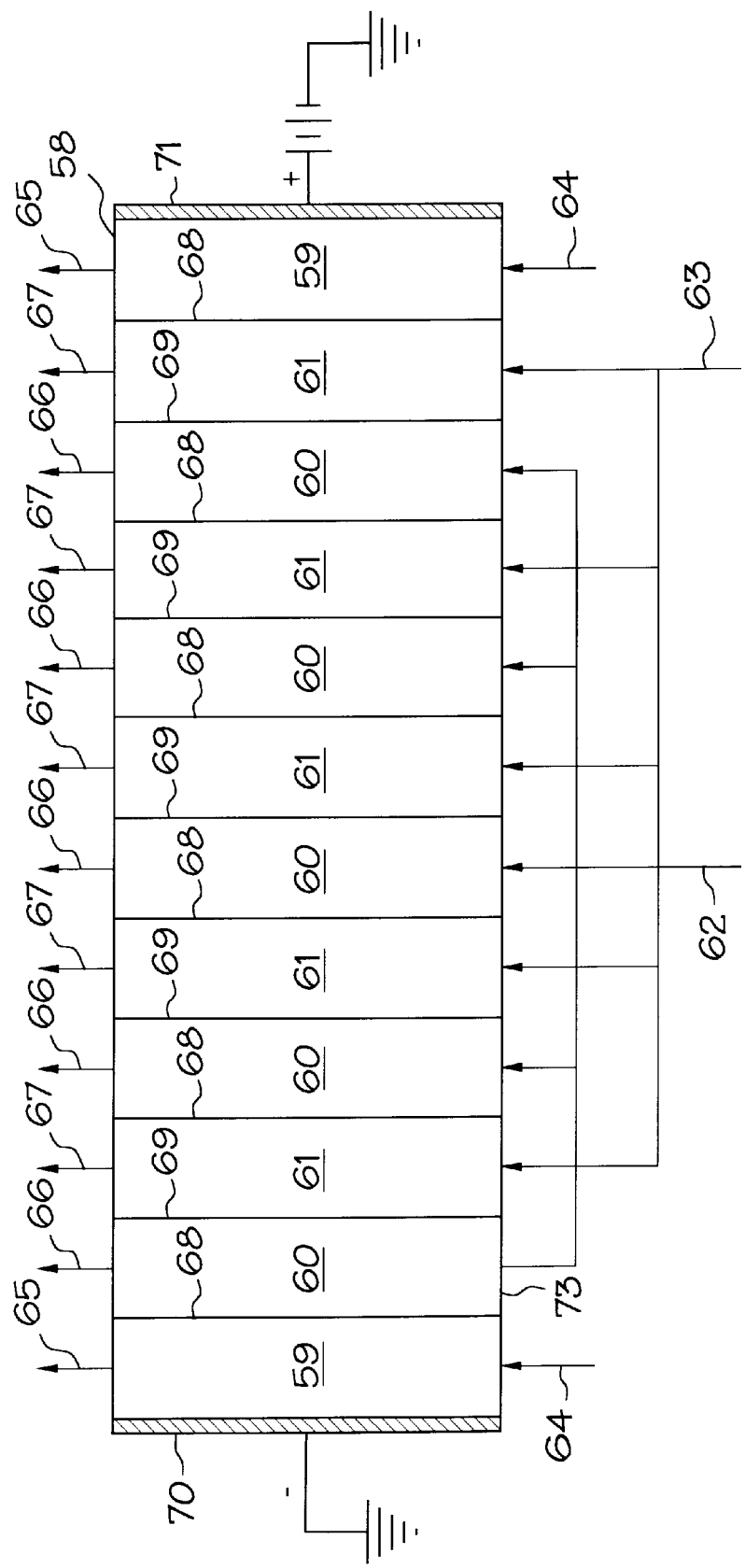
FIG. 7 is a schematic drawing of an electrodialysis apparatus.

In electrodialysis the permeate is introduced into an apparatus comprising a number (stack) of compartments having alternating side walls formed from anionic and cationic membranes (See FIG. 7).

FIG. 7 is a schematic representation of an electrodialysis cell stack. Electrodialysis cell stack 58 comprises a series of compartments 59, 60, and 61 formed by anionic membranes 69 and cationic membranes 68 arranged in a liquid tight container 73. Positive electrode 71 and negative electrode 70 are arranged to be in contact with an electrodynamic solution in compartments 59. In the electrodialysis experiments the electrode rinse solution was 0.5 normal sulfuric acid and was pumped into the compartments 59 through line 64 and returned to rinse solution storage through line 65.

The permeate containing sulfuric acid was pumped into compartments 60 through line 62 and was returned to the feed tank through line 66. A conductive water solution of sulfuric acid was pumped into compartments 61 through line 63 and returned to sulfuric acid storage through line 67.

A direct current was applied to the cell stack with electrode 71 being positive and electrode 70 being negative. The sulfate anions in the permeate pass through anionic membranes 69 in the direction of the positive electrode and enter compartment 61. The sulfates in the permeate is reduced. The organic mono-and di-sulfonates do not pass readily through the anionic membrane and remain with the permeate. The permeate was circulated through the chambers 60 until the sulfate is reduced to the required level. When the sulfate level in the permeate becomes low (about 0.5% by weight) the (alkyl) naphthalene mono- and di-sulfonates begin to be transported across the anionic membrane and collect in the sulfuric acid in compartments 61.

Alternating compartments contain permeate and the compartments in between contain water; the cells adjacent to the electrodes generally contain an electrolyte to protect the electrodes. A direct current is applied across the stack of compartments. The positive electrode is arranged at the side with the anionic membrane and the negative electrode is arranged at the side of the cationic membrane. When the direct current is applied, the anions, mostly sulfate, flow through the anionic membrane to the compartment containing water and the cations, mostly protons, flow through the cationic membrane to the compartment containing water. Since the organic material has a high molecular weight, and even though it has an anionic charge, only a small amount passes through the anionic membrane because of the relatively large size of the organic molecules.

The separated sulfuric acid can be concentrated by evaporation mixed with oleum and returned to the sulforation step of the process.

TABLE 1

NEUTRALIZED PRODUCT

| | | | | | | Na₂SO₄ | Product | Na₂SO₄ | | Permeate | | | | |
|---|---|---|---|---|---|---|---|---|---|---|---|---|---|---|
| Batch | Feed Volume Liters | Feed Rate Liter/hr | Feed Temperature °C. Range | Feed Solids % by Weight | % of solids in Feed by Wt. | Volume Liters (retentate) | Product Solids % by Weight | % of Solids by wt. of Product | Volume Liters | % Na₂SO₄ by wt. of Permeate | % Organic material by wt. of Permeate | Permeate Flow rate Liters/day/ Ft² avg | Feed Pressure psig Range | Treatment time Hours |
| 15 | 276 | 1040 | 48/51 | 36.1 | 11.1 | 191 | 36.8 | 2.4 | 194 | 4.4 | N/A | 13.6 | 275/409 | 20.2 |
| 16 | 244 | 1040 | 45/51 | 34.9 | 10.9 | 200 | 36 | 1.7 | N/A | N/A | N/A | N/A | 350/395 | 24.4 |
| 17 | 265 | 1040 | 44/52 | 34.2 | 9.9 | 237 | 33.5 | 3.0 | 196 | 3.4 | N/A | 17.9 | 356/378 | 15.5 |
| 19 | 257 | 1040 | 48/55 | 33.8 | 11.5 | 170 | 37.6 | 0.5 | 286 | 2.4 | 1.5 | 13.4 | 362/416 | 30.2 |
| 20 | 234 | 1040 | 48/55 | 36.0 | 11.7 | 174 | 42.2 | 1.9 | 240 | 3.3 | 1.6 | 15.2 | 360/410 | 22.4 |
| 21 | 240 | 1040 | 49/53 | 36.9 | 10.6 | 184 | 39.3 | 1.9 | 238 | 4.5 | N/A | 18.6 | 360/375 | 18.1 |

NA—Not Available

TABLE 2

ACID (UNNEUTRALIZED) REACTION PRODUCT

| | | | | | | | H₂SO₄ | Product | H₂SO₄ | | Permeate | | | |
|---|---|---|---|---|---|---|---|---|---|---|---|---|---|---|
| Batch | Feed Volume Liters | Feed Rate Liter/ | Feed Temperature °C. Range | Feed Pressure PSIG Range | Feed Solids % by weight | % of solids of Feed by wt. | Volume Liters (Retentate) | Product Solids % by weight | % of solids in Product by wt. | Volume Liters | % H₂SO₄ by wt. of Permeate | % organic material by wt. of Permeate | Permeate Flow Rate Liter/day/ FT² | Treatment Time Hours |
| 24 | 147 | 810/1094 | 40/54 | 364/382 | 29.4 | 9.2 | 87 | 28.7 | 0.4 | 150 | N/A | 2.1 | 6 | 24.8 |
| 25 | 189 | 707/874 | 35/51 | 378/403 | 32.8 | 8.2 | 153 | 31.6 | 1.5 | 136 | 3.38 | 2.1 | 5.1 | 26.6 |
| 26 | 163 | 740/837 | 37/50.5 | 394/440 | 35.5 | 8.6 | 185 | 36.7 | 6.1 | 23 | 6.9 | N/A | 1.7 | 13.8 |
| 27 | 183 | 731/1102 | 45/56.2 | 433/441 | 37.1 | 9.1 | 127 | 33.5 | 1.1 | 146 | 6.7 | 2.5 | 3.9 | 38 |
| 28 | 246 | 924/1350 | 42/52 | 440/441 | 26.8 | 18.8 | 133 | 35.2 | 0.2 | 113 | 4.14 | 5.0 | 2.4 | 46.7 |

NA—Not Available

EXAMPLE 2

A sample of SELLOGEN™ 6067A an (alkyl) naphthalene sulfonate was treated by nanofiltration in a tubular shaped membrane by a diafiltration procedure. The composition was a solution in water containing sulfate in the form of its sodium salt. 30% and 40% by weight solids solution were treated. The nanofiltration membrane had an area of 0.25 Ft² and was an MPT 34A type as used in the previous experiments. The parameters and results of the experiments are shown in Table 3.

EXAMPLE 3

Samples of an (alkyl) naphthalene sulfonate-formaldehyde condensation product were prepared. The amount of (alkyl) naphthalene mono- and di-sulfonate in the samples was varied. The samples were compared to a commercial product (standard) which contained about 10% by weight of the solids of the (alkyl) naphthalene mono- and di-sulfonate. The remainder of the samples were similar in relation to the amounts of low, medium and high molecular weight condensation species (with the exception of the data

TABLE 3

| EXAMPLE | PRODUCT | SOLIDS WGHT % | PRESS. PSIG (AVG.) | TEMP. °C. | FLOW (AVG) LITERS\HR. | PERMEATE VOLUME ml | PERMEATE FLOW mls/min | H2SO4* EQUIVALENT WGHT % IN PERMEATE |
|---|---|---|---|---|---|---|---|---|
| 3A | SELLOGEN 6067A | 40% | 426 psig | 50 | NA | 94 | 1.4 | 3.6 |
| 3B | SELLOGEN 6067A | 30% | 420 psig | 54 | 1325 L/H | 59 | 1.9 | 5.9 |

The data illustrates that the sulfate can be removed from at alkyl naphthalene sulfonate which is not condensed with an aldehyde, by a monofiltration procedure.

parts marked with a star which had a portion of the low molecular oligomers removed). The materials with the higher percentage of the uncondensed (alkyl) naphthalene mono- and di-sulfonates than the standard were prepared by adding (alkyl) naphthalene mono- and di-sulfonates in the ratio in the sample to the sample.

Concrete was prepared using 18.7 grams of the (alkyl) naphthalene sulfonate-formaldehyde dispersing agent per batch which required 5,361.6 grams of cement. The slump of the concrete as prepared (0 minutes) and after 20 minutes additional mixing was measured.

Figure 6A:
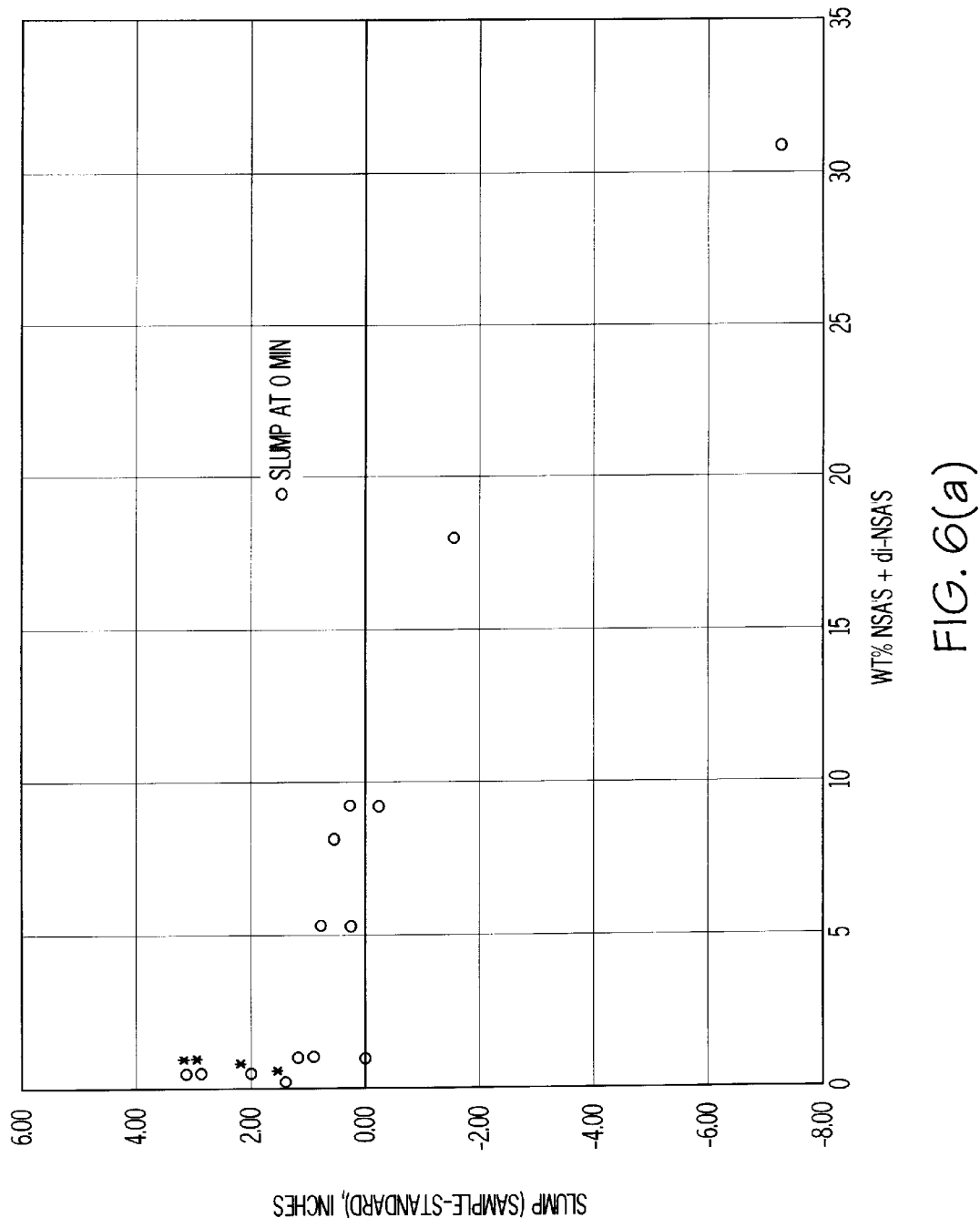
FIGS. 6(a) and (b) are plots of the difference between slump of concrete as a function of (alkyl) naphthalene mono- and di-sulfonates in the (alkyl) naphthalene sulfonic acid formaldehyde condensate.

FIG. 6(a) is a plot of value of the initial slump of the concrete (0 minutes) prepared using the samples with varying amounts of (alkyl) naphthalene mono- and di-sulfonate minus the initial slump of the concrete prepared using the standard sample against the % by weight of (alkyl) naphthalene mono- and di-sulfonates.

FIG. 6(b) is a plot of the value of the 20 minute slump of the concrete prepared using the samples with varying amounts of (alkyl) naphthalene mono-and di-sulfonates minus the 20 minute slump of concrete prepared using the standard (alkyl) naphthalene sulfonate-aldehyde condensation product.

The plots clearly show that the (alkyl) naphthalene sulfonate-aldehyde condensation product with a reduced content of (alkyl) naphthalene mono- and di-sulfonates provides increased slump for concrete. The increase in slump is particularly apparent in the 20 minute slump values. In some cases an increase in 20 minute slump values of more than 50% can be achieved with materials containing less than about 2% by weight of the solids of (alkyl) naphthalene mono- and di-sulfonates.

A decrease in the amount of low molecular weight oligomers in the (alkyl) naphthalene sulfonate-aldehyde condensate also increases the slump values of concrete containing the dispersant. Slump is an indication of the fluidity or flowability of the concrete. Large slump values at 20 minutes is a clear indicator that the cement is more easily worked and if desired, the amount of water in the concrete formulation can be reduced to provide a concrete with equivalent workability.

EXAMPLE 4

Samples of permeate from monofiltration of an unneutralized (alkyl) naphthalene sulfonate-formaldehyde condensate composition was subjected to electrodialysis in the stack of cells (TS-1-10 cell stack purchased from Tokuyama America Corp.) which had AMX anionic membranes and CMX cationic membranes spaced 0.6–0.7 mm apart. Permeate feed to the unit diluate was circulated through alternate cells. In adjacent cells, a dilute sulfuric acid solution (concentrate) was circulated. A 0.5 normal sulfuric acid rinse solution was pumped through the cells adjacent to the electrodes. The example was done in a batch method. FIG. 7 is an illustration of a typical electrodialysis cell stack.

When an electric current was applied through the cell stack, the sulfate anions passed through the anionic membrane and into the recirculating concentrate stream. The amount of sulfate in the diluate was reduced and the sulfate content of the concentrate increased. The diluate feed was circulated through the cells at constant voltage. As the amount of sulfate in the feed decreased from 7 milliamperes/$cm^2$ initially to about 2–3 milliamperes/$cm^2$ the selectivity for the sulfate ion over the organic mono- and di-sulfonate was excellent; substantially no organic mono-and di-sulfonates passed through the anionic membranes until the current reached the range of about 2–3 milliamperes/$cm^2$.

Figure 8:
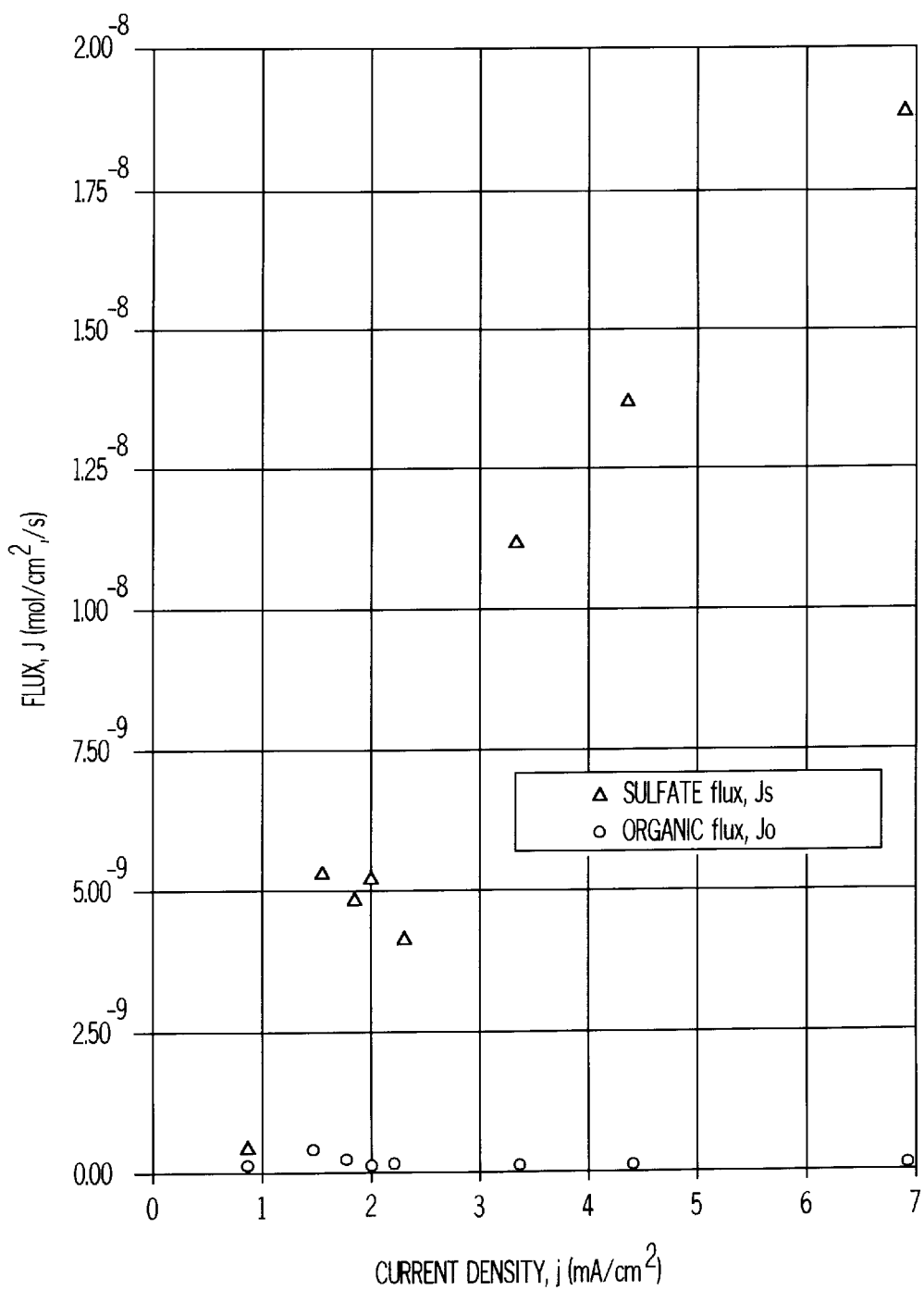
FIG. 8 is a plot of $SO_4$ flux and (alkyl) naphthalene sulfonic and mono- and di-sulfonate against current flow in an electrodialysis apparatus.
Figure 9:
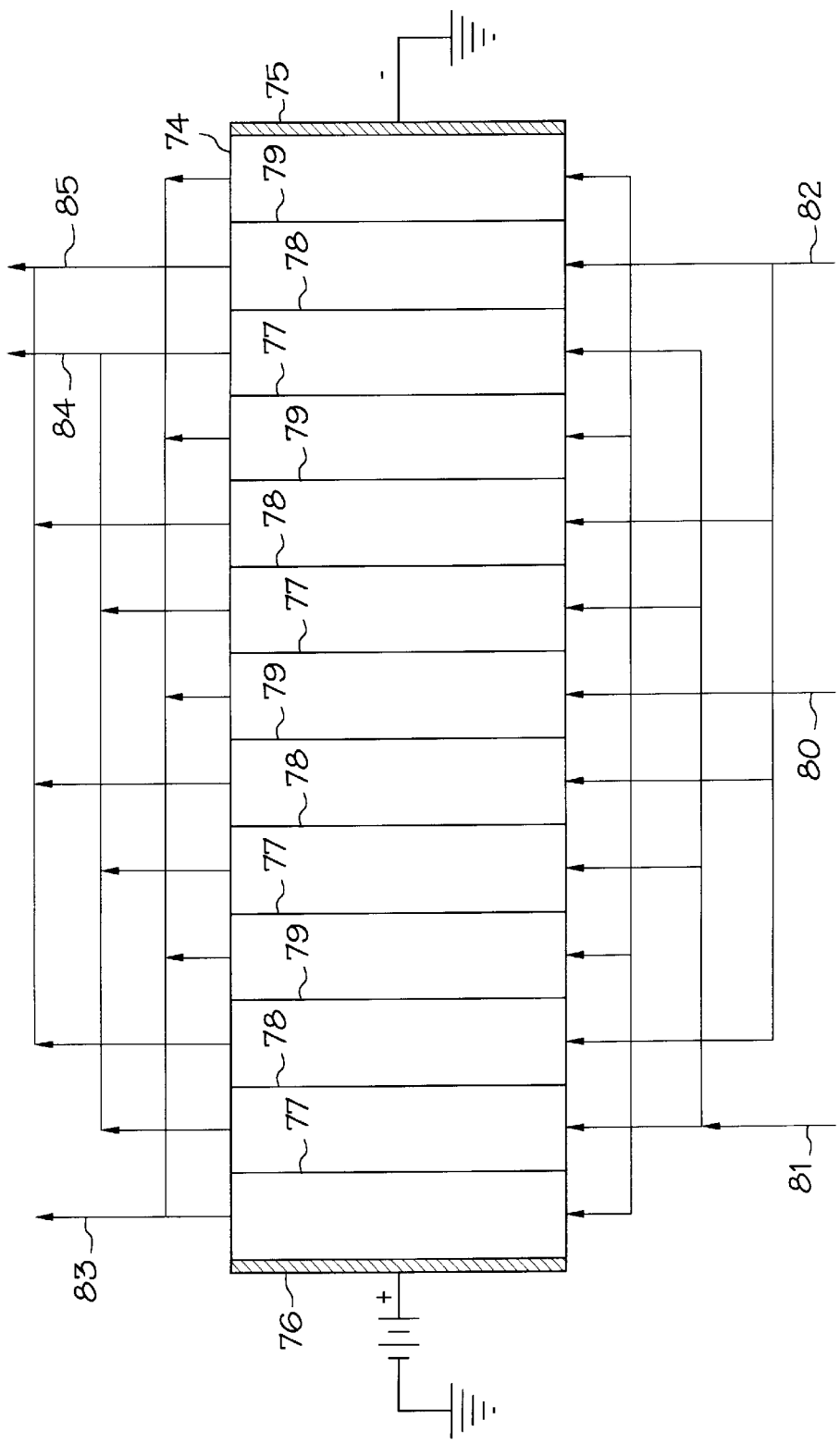
FIG. 9 is a schematic drawing of a bipolar electrodialysis apparatus.

FIG. 8 is a graph showing the flux rate for sulfate ion and the (alkyl) naphthalene sulfonates in the diluate feed to the electrodialysis cells. As can be seen from the graph, the organic sulfonate flux is very low which indicates that a clean separation between the sulfuric acid and the acid sulfonates can be obtained by electrodialysis.

EXAMPLE 5

Permeate obtained by diafiltration of a neutralized (sodium salt) of an (alkyl) naphthalene sulfonate-formaldehyde condensation product (LOMAR 1487H a product of Henkel Corp.) over a MPS 34A nanofiltration membrane was treated by ion exchange to separate the sulfate from the (alkyl) naphthalene sulfonates in the permeate.

A one (1) inch diameter by four (4) inch long column was packed with a bed of AmberliteC IRA-35- a weak base anion exchange resin. The permeate which contained 2.1% sulfate and 1.1% (alkyl) naphthalene sulfonates was passed through the bed (30 volumes of permeate for one volume of resin). The (alkyl) naphthalene sulfonates were absorbed by the resin. The resin capacity was 4.8 pounds of (alkyl) naphthalene sulfonate per cubic foot of resin.

The resin was regenerated by a 4% weight NaOH solution. Ninety three (93) percent of the absorbed (alkyl) naphthalene sulfonates were recovered.

On a water and NaOH free basis, the regenerating solution after contact with the resin contained 98% by weight (alkyl) naphthalene sulfonates and 2% by weight $Na_2SO_4$ based on the weight of (alkyl) naphthalene sulfonates and $Na_2SO_4$ in the regenerating solution.

Ion exchange can be effectively used to separate soluble sulfate salts from a solution of sulfate salts and (alkyl) naphthalene sulfonates.

Other ion exchange resins were tested and it was discovered that strong ion exchange resins absorb sulfate ions so that the selectivity for separation of the sulfate from the organic sulfonates decreases as the basicity of the resins increase. Low basicity ion exchange resins, due to their excellent selectivity and easy regeneration are preferred for use in the present invention.

EXAMPLE 6

A bipolar electrodialysis apparatus can be used to separate sulfate salts from the permeate produced by nanofiltration of organic sulfonate/sulfate materials. A diagrammatic representation of a bipolar electrodialysis apparatus is shown in FIG. 8.

A bipolar electrodialysis unit 74 comprises cationic membranes 77, bipolar membranes 78 and anionic membranes 79 arranged in series to separate the unit 74 into a series of separate cells which are narrow in relation to the area of the membrane. A direct current is applied across the membrane stack by electrodes 75 and 76. The feed to the unit (diluate), which is to be treated, is circulated to the cells formed between the anionic and cationic membranes through line 80 and is removed through line 83. A caustic solution is circulated between the cationic membrane 77 and the bipolar membrane 78 through line 81 and removed from the cell through line 84. A sulfuric acid solution is circulated through the cell formed between anionic membrane 79 and bipolar membrane 78 through line 82 and removed through line 85.

In the cell between the cationic membrane and the bipolar membrane NaOH is formed when direct current flows through the cell and is removed through line 84. The concentration of NaOH in the stream is increased.

In the cell between the anionic membrane and the bipolar membrane, sulfuric acid is formed and the strength of the sulfuric acid stream is increased. The sulfuric acid is removed through line 85. The feed (diluate) stream is reduced in sodium sulfate content and is removed from the cell through line 83. The organic sulfonates do not readily permeate the membranes and remain in the diluate stream. When the sodium sulfate has been reduced to the desired level, the diluate can be returned to the process at the condensation zone or as feed to the nanofiltration zone.

The sulfuric acid stream can be concentrated and mixed with oleum as feed to the sulfation zone. The sodium hydroxide can be used to neutralize and dilute the condensation product. Using a bipolar electrodialysis cell, it is possible to substantially reduce waste formed by the process for producing organic sulfonate/sulfate materials and particularly (alkyl)aryl sulfonate-aldehyde condensation products.

Figure 4A:
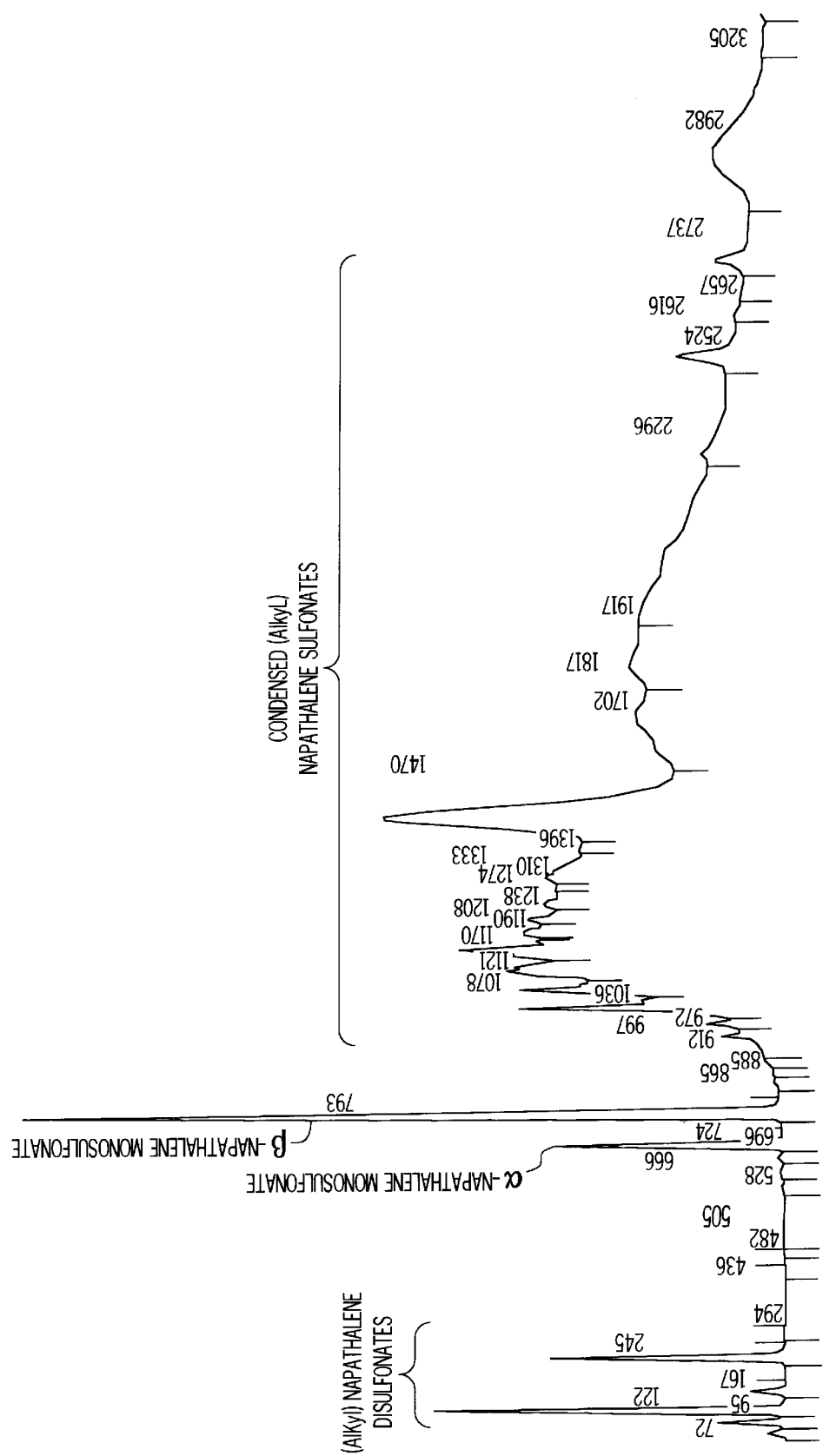
FIG. 4a is a chromatograph of a typical naphthalene sulfonate-formaldehyde condensation product.
Figure 4B:
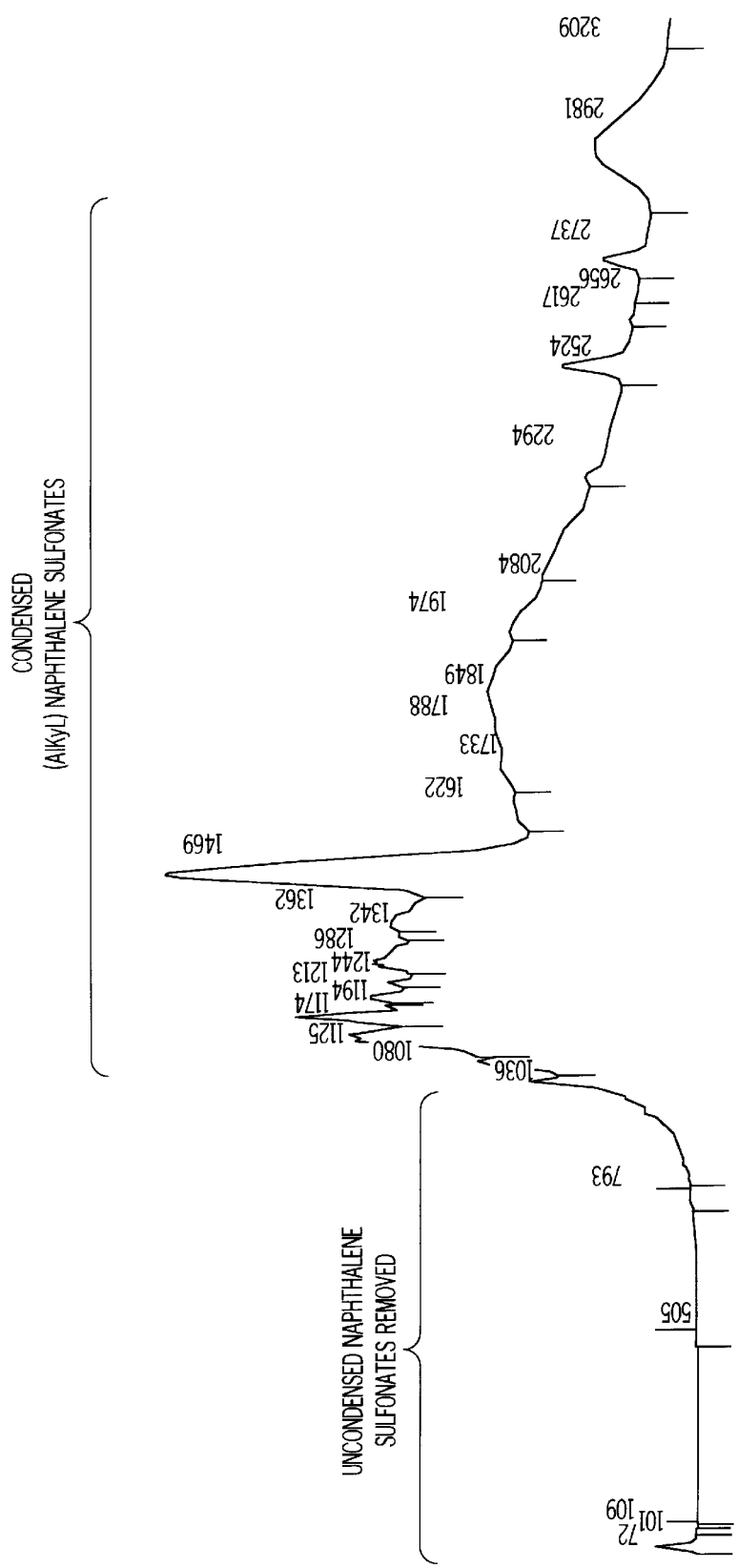
FIG. 4b is a chromatograph of a naphthalene sulfonate formaldehyde condensation product which has been treated by the nanofiltration process of the invention without recycle of the uncondensed mono-sulfonates, di-sulfonates and lower oligomers.

FIG. 4(a) is a HPL chromatogram of an (alkyl) naphthalene sulfonate-formaldehyde condensation product containing (alkyl)naphthalene nano- and di-sulfonates. FIG. 4(b) is an HPL chromatogram of an (alkyl)naphthalene sulfonate-aldehyde condensation product. Comparison of the chromatogram shows that it is possible to remove substantially all the (alkyl) naphthalene mono-and di-sulfonates from the mixture without substantially affecting the polymeric materials by a nanofiltration process. The product with the (alkyl) naphthalene mono- and di-sulfonates removed would also have a low salt or acid content. The product with the low salt or acid content and low (alkyl) naphthalene mono- and di-sulfonate content has improved dispersion ability for concrete and can be used in the ultra strength concrete formulations.

The invention has been described in relation to removing sulfate and lower molecular weight ionic materials from an (alkyl) naphthalene sulfate-formaldehyde condensation product or an (alkyl) naphthalene sulfonate. However, the process can be utilized to remove sulfate and low molecular weight materials from other sulfated or sulfonated organic compositions such as sulfated alcohols, sulfated alkoxylated fatty alcohols or fatty acids and condensation products of aromatic sulfonates and aldehydes.

The process of the invention produces low amounts of waste materials which must be disposed of and permits recycle of the organic components to the process for recover and use.

The normal material with low salt and (alkyl) naphthalene sulfonate aldehyde condensation products have unexpectedly found to provide dispersants which produce high strength concrete with large slump values.

EXAMPLE 7

A bipolar electrodialysis apparatus similar to that shown in FIG. 8 is used to separate the sulfate from the permeate obtained by nanofiltration of a crude unneutralized (alkyl) naphthalene sulfonate-formaldehyde condensation product. The bipolar electrodialysis apparatus is modified by replacing the cathodic membranes with anionic membranes.

The permeate obtained by nanofiltration of a crude unneutralized (alkyl) naphthalene sulfonate-formaldehyde condensation product contains about 4% by weight of sulfuric acid and about 1% by weight of (alkyl) naphthalene mono- and di-sulfonates.

The permeate feed (diluate) is recirculated through a cell between anionic membrane and a bipolar membrane. A sulfuric acid stream is circulated through the cells on both sides of the cell through which the diluate is circulated.

When a direct currents is applied across the cells, sulfate ions permeate from the diluate through the anionic membrane into the sulfuric acid stream and the side of the cell nearest the positive electrode. At the bipolar membrane $H_2O$ is split into $H^+$ and $OH^-$. The $H^+$ permeates the membrane toward the negative electrode and the $OH^-$ permeates toward the positive electrode to react with the $H^+$ ions in the diluate to form $H^2O$.

The sulfonate is removed from the diluate and forms a sulfuric acid stream which can be concentrated and mixed with oleum to sulfurate the starting material.

EXAMPLE 8

Samples were prepared by nanofiltration of a standard (alkyl) naphthalene sulfonate-aldehyde condensation product dispersant 1487-H (a commercial product). The commercial product contained about 10% by weight of sodium sulfate. The commercial product was desalted by nanofiltration to provide samples with reduced sodium sulfate content. The nanofiltration was done in a manner to leave the amount of (alkyl) naphthalene mono- and di-sulfonates substantially unchanged.

The concrete was prepared according to the following formulate:

| | |
|---|---|
| Cement | 54662 grams |
| Sand | 10932 grams |
| Stone | 8231 grams |
| Water | 2119 grams (includes water from all sources) |
| Dispersant | 19.12 grams |

The dry ingredients were placed in a cement mixer, about ½ of the required water added and the materials mixed for two minutes. The remaining water was added and the concrete mixed for an additional two minutes.

The slump of a sample of the concrete was measured according to ASTM C143. The slump is the initial slump or 0 minutes. The concrete is returned to the mixer and mixed for an additional twenty minutes and the slump again measured according at ASTM C143. The results of the tests are shown in Table 4.

TABLE 4

| | Slump | |
|---|---|---|
| Sample | 0 Minutes | 20 Minutes |
| 1487H Std. | 8.0 | 5.50 |
| 1887Y | 11.0 | |
| CU17117 | 10.0 | 9.0 |

1887Y contained 0.5% $CaSO_4$ and about 2% $Na^2CO^3$
CU17117 was 1487H desalted by nanofiltration The data clearly illustrates that a reduction in sodium sulfate improves the performance of the dispersant.

A second sample was prepared by nanofiltration of a sample of the acid from a commercial dispersant LOMAR 18874. The LOMAR 1887Y after neutralization contained 0.5% $CaSO_4$ and about 2% $NaCO_3$ based on the weight of solids. Product 5 contained 1.12% by of solids of $Na_2SO_4$. The standard material LOMAR 1487H was also included in the test. The results of the tests are shown in Table 5.

TABLE 5

| | Slump | | 24 hour Compression |
|---|---|---|---|
| Sample | 0 Minutes | 20 Minutes | Strength in Pounds |
| 1487H | 6 | 4.25 | 24,333 |
| Product 5 | 9 | 6 | 27,500 |
| 1887Y | 8.25 | 5.5 | 23,333 |

The data illustrates the improvement in slump and compressive strength imparted to concrete by the low salt product (Product 5).

What is claimed is:

1. A process for producing a low sulfate organic sulfonate/sulfate aqueous solution from a soluble sulfate containing sulfonate/sulfate which comprises:

forming an aqueous solution of organic sulfonate/sulfate; and passing the aqueous solution of the organic sulfonate/sulfate containing the soluble sulfate over a nanofiltration zone at an elevated pressure to form a retenate with a reduced sulfate content and a permeate containing the soluble sulfate and organic material, said nanofiltration zone comprising a membrane that has been prepared by contacting the membrane with a solution of dilute nitric acid and subsequently contacting the membrane with an alkaline solution of a chelating agent.

2. The process of claim 1 further including the step of passing the permeate to a permeate treating zone and separating the sulfate from the permeate to provide a first aqueous stream containing the sulfate and a second aqueous stream containing organic material.

3. The process of claim 2 further including the step of recycling at least a portion of at least one of the first stream and second stream to the process for forming the aqueous solution of the organic sulfonate/sulfate.

4. The process of claim 1 wherein the nanofiltration zone includes a membrane which retains materials having a molecular weight greater than a molecular weight cut-off and said cut-off is about 600 to 1000.

5. The process of claim 4 wherein said cut-off is about 150 to 250.

6. The process of claim 4 wherein said membrane includes a hydrophilic surface and said aqueous solution is passed over the hydrophilic surface at a pressure of about 100 to about 700 psi.

7. The process of claim 6 wherein said membrane is a spiral wound unit.

8. The process of claim 4 wherein water is added to said aqueous solution as said solution is passed over said membrane.

9. The process of claim 4 wherein said step of passing said aqueous solution over said membrane is conducted at a temperature of about 35 to 80° C., and the pressure drop across said membrane is about 200 to 400 psi.

10. The process of claim 2 wherein the sulfate is present in the permeate in the form of sulfuric acid and said step of separating the sulfate from the permeate includes subjecting the permeate to electrodialysis and removing sulfuric acid from said permeate.

11. The process of claim 10 wherein said process additionally includes the step of concentrating said sulfuric acid to about 50 to 80% by weight.

12. The process of claim 11 wherein said process additionally includes the step of recycling the concentrated sulfuric acid for use in said step of forming said solution of said organic sulfonate/sulfate.

13. The process of claim 2 wherein the sulfate is present in the permeate in the form of a salt and said step of separating the sulfate from the permeate includes subjecting the permeate to ion exchange.

14. The process of claim 1 wherein said organic sulfonate/sulfate is selected from the group consisting of sulfated alkaline oxide adducts, sulfated and partially esterified polyhydric alcohols, alkyl sulfonates, alkyl sulfates, sodium dialkyl sulfosuccinates, alkyl benzene sulfonates, condensation products of (alkyl)naphthalene sulfonic acid and formaldehyde, condensation products of ditolyether formaldehyde and sulfuric acid, condensation products of chloromethylated diphenylene, (alkyl)naphthalene and sulfuric acid, condensation products of mononuclear aromatic compounds and formaldehyde, (alkyl)naphthalene sulfonic acids and optionally sodium sulfite, or condensation products of (alkyl)naphthalene, toluene formaldehyde and sulfuric acid.

15. The process of claim 14 wherein said organic sulfonate/sulfate is an aldehyde condensation product of an alkylbenzene sulfonic acid and/or an alkyl naphthalene sulfonic acid wherein the alkyl moiety contains 1 to 18 carbon atoms.

16. The process of claim 15 wherein said aldehyde condensation product is a condensation product of formaldehyde and alkylnaphthalene sulfonic acid.

17. A method for improving the permeability of a nanofiltration membrane for soluble salts in an aqueous solution of organic sulfonate/sulfate which comprises:

contacting the nanofiltration membrane with a dilute nitric acid solution and with an alkaline solution of a chelating agent.

* * * * *